(12) United States Patent
Kennedy et al.

(10) Patent No.: US 10,064,741 B2
(45) Date of Patent: Sep. 4, 2018

(54) CLAMPING DEVICE FOR AFFIXING A STOP PLATE TO AN INTERBODY IMPLANT

(71) Applicant: Titan Spine, LLC, Mequon, WI (US)

(72) Inventors: Eric Kennedy, Wauwatosa, WI (US); Charles J. Turner, Milwaukee, WI (US); Peter F. Ullrich, Jr., Neenah, WI (US)

(73) Assignee: Titan Spine, Inc., Mequon, WI (US)

( * ) Notice: Subject to any disclaimer, the term of this patent is extended or adjusted under 35 U.S.C. 154(b) by 0 days.

(21) Appl. No.: 14/980,725

(22) Filed: Dec. 28, 2015

(65) Prior Publication Data

US 2017/0181869 A1 Jun. 29, 2017

(51) Int. Cl.
*A61F 2/46* (2006.01)
*A61F 2/44* (2006.01)

(52) U.S. Cl.
CPC .......... *A61F 2/4611* (2013.01); *A61F 2/4455* (2013.01); *A61F 2/4637* (2013.01); *A61F 2002/4638* (2013.01)

(58) Field of Classification Search
CPC .................. A61F 2/4637; A61F 2/4611; A61F 2002/4622; A61F 2002/4628
See application file for complete search history.

(56) References Cited

U.S. PATENT DOCUMENTS

| | | | |
|---|---|---|---|
| 2,821,762 A * | 2/1958 | Foose | A47C 1/124 24/115 G |
| 6,972,019 B2 | 12/2005 | Michelson | |
| 7,056,321 B2 | 6/2006 | Pagliuca et al. | |
| 7,179,225 B2 | 2/2007 | Shiuzas et al. | |
| 7,226,451 B2 | 6/2007 | Shiuzas et al. | |
| 7,442,209 B2 | 10/2008 | Michelson | |
| 7,637,952 B2 | 12/2009 | Landry et al. | |
| 7,645,232 B2 | 1/2010 | Shluzas | |
| 7,651,496 B2 | 1/2010 | Keegan et al. | |
| 7,655,012 B2 | 2/2010 | DiPoto et al. | |
| 7,658,739 B2 | 2/2010 | Shluzas | |
| 7,691,120 B2 | 4/2010 | Shluzas et al. | |
| 7,736,305 B2 | 6/2010 | DiPoto | |
| 7,740,649 B2 | 6/2010 | Mosca et al. | |
| 7,794,502 B2 | 9/2010 | Michelson | |
| 7,850,695 B2 | 12/2010 | Pagliuca et al. | |
| 7,909,859 B2 | 3/2011 | Mosca et al. | |
| 7,942,903 B2 | 5/2011 | Moskowitz et al. | |
| 7,976,464 B2 | 7/2011 | Shluzas et al. | |
| 8,016,828 B2 | 9/2011 | Shluzas | |
| 8,157,844 B2 | 4/2012 | Gimbel et al. | |
| 8,162,994 B2 | 4/2012 | Gimbel et al. | |
| 8,167,946 B2 | 5/2012 | Michelson | |
| 8,182,514 B2 | 5/2012 | Gimbel et al. | |

(Continued)

*Primary Examiner* — Julianna N Harvey

(74) *Attorney, Agent, or Firm* — Stradley Ronon Stevens & Young, LLP

(57) ABSTRACT

A system for affixing a stop plate to an interbody implant. The system includes a clamping device, a stop plate, and an inserter tool. The clamping device includes a body, a first clamping portion attached to the body including a stepped seat and a guide slot, and a second clamping portion attached to the body by a spring. Compressing the spring moves the second clamping portion away from the first clamping portion and expanding the spring moves the second clamping portion toward the first clamping portion.

20 Claims, 16 Drawing Sheets

(56) References Cited

U.S. PATENT DOCUMENTS

| | | |
|---|---|---|
| 8,187,330 B2 | 5/2012 | Gimbel et al. |
| 8,267,965 B2 | 9/2012 | Gimbel et al. |
| 8,328,872 B2 | 12/2012 | Duffield et al. |
| 8,353,913 B2 | 1/2013 | Moskowitz et al. |
| 8,425,602 B2 | 4/2013 | Guyer et al. |
| 8,523,912 B2 | 9/2013 | Gimbel et al. |
| 8,523,930 B2 | 9/2013 | Saunders et al. |
| 8,608,651 B2 | 12/2013 | Shluzas |
| 8,623,019 B2 | 1/2014 | Perrow et al. |
| 8,641,768 B2 | 2/2014 | Duffield et al. |
| 8,668,741 B2 | 3/2014 | Michelson |
| 8,709,083 B2 | 4/2014 | Duffield et al. |
| 8,864,785 B2 | 10/2014 | Pagliuca et al. |
| 8,979,749 B2 | 3/2015 | Gorek et al. |
| 9,005,293 B2 | 4/2015 | Moskowitz et al. |
| 9,084,636 B2 | 7/2015 | Mekhail et al. |
| 2006/0287652 A1* | 12/2006 | Lessig .................. A61B 17/645 606/54 |
| 2010/0145459 A1 | 6/2010 | McDonough et al. |
| 2010/0145460 A1 | 6/2010 | McDonough et al. |
| 2013/0268008 A1 | 10/2013 | McDonough et al. |
| 2015/0216675 A1 | 8/2015 | McDonough et al. |

* cited by examiner

CLAMPING DEVICE FOR AFFIXING A STOP PLATE TO AN INTERBODY IMPLANT

FIELD OF THE INVENTION

The invention relates generally to the field of medical interbody implants. In particular, the invention relates to an apparatus for affixing a stop plate to an interbody implant.

BACKGROUND OF THE INVENTION

Various publications, including patents, published applications, technical articles and scholarly articles are cited throughout the specification. Each of these cited publications is incorporated by reference herein, in its entirety and for all purposes.

In simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

In order to secure the implant between the opposing endplates, one or more fixation devices are typically used to stabilize the implant and prevent movement of the implant after surgery. For example, one or more screws may be inserted such that the screws extend through the implant and engage with one or more bone surfaces adjacent to the implant. Installation of such fixation devices, however, typically requires drilling or awling processes that subject the implant to forces that may cause the implant to be displaced from its original intended position. Traditional spinal implants generally address this challenge by including teeth on one or more surfaces of the implant that engage with adjacent bone and hold the implant in place. Teeth can damage the structural integrity of the vertebral endplates, however, and cause the spinal fusion to fail. Accordingly, there is a need for a way to stabilize an implant, while securing the implant with fixation devices, that does not require teeth.

SUMMARY OF THE INVENTION

The invention features a clamping device for affixing a stop plate to an interbody implant. The clamping device includes a body, a first clamping portion attached to the body including a stepped seat and a guide slot, and a second clamping portion attached to the body by a spring. The second clamping portion is movable with respect to the first clamping portion. Compressing the spring moves the second clamping portion away from the first clamping portion and expanding the spring moves the second clamping portion toward the first clamping portion. The clamping device may further include one or more anti-slipping elements. The anti-slipping elements may be rubber or silicone feet. The clamping device may further include a caddy for storing a stop plate.

The invention further features a system for securing an interbody implant including a clamping device, an implant, a stop plate, and an inserter tool. The clamping device includes a body, a first clamping portion attached to the body including a stepped seat and a guide slot, and a second clamping portion attached to the body by a spring. The second clamping portion is movable with respect to the first clamping portion. Compressing the spring moves the second clamping portion away from the first clamping portion and expanding the spring moves the second clamping portion toward the first clamping portion. The implant includes an internally threaded central hole and a fixation element. The stop plate includes an externally threaded end sized to fit in the central hole of the implant, an internally threaded end, and a free spinning plate attached to the central shaft between the externally threaded end and the internally threaded end. The free spinning plate is sized to fit within the guide slot of the clamping device. The inserter tool includes a hollow outer shaft and inner shaft inside the outer shaft which can rotate with respect to the outer shaft. The inner shaft includes an externally threaded engaging end which is sized to fit the internally threaded end of the stop plate. The clamping device may further include one or more anti-slipping elements. The anti-slipping elements may be rubber or silicone feet. The clamping device may further include a caddy for storing a stop plate. The fixation element of the implant may be a hole adapted to allow a screw to pass through the implant and engage an adjacent bone surface. The screw may also be included in the system. An open end of the hollow outer shaft of the inserter tool may be sized to fit over the internally threaded end of the stop plate and may be shaped to engage with the exterior of the internally threaded end. The open end and the internally threaded end may both be hexagonal.

The invention further features a method of affixing a stop plate to an interbody implant. The method includes providing a clamping device, a stop plate, an implant, and an inserter tool. The clamping device includes a body, a first clamping portion attached to the body including a stepped seat and a guide slot, and a second clamping portion attached to the body by a spring. The second clamping portion is movable with respect to the first clamping portion. The stop plate includes a central shaft having an externally threaded end and an internally threaded end, and a free spinning plate attached to the central shaft between the externally threaded end and the internally threaded end. The implant includes an internally threaded hole. The inserter tool includes a hollow outer shaft, and an inner shaft inside the outer shaft which can rotate with respect to the outer shaft and has an externally threaded engaging end. The spring is compressed to move the second clamping portion away from the first clamping portion. The implant is then inserted between the first clamping portion away from the first clamping portion with the implant aligned with the stepped seat and the internally threaded hole facing up. The spring is then expanded to move the second clamping portion away from the first clamping portion and secure the implant between the first clamping portion and the second clamping portion. The engaging end of the inserter tool is engaged with the internally threaded end of the stop plate by to rotating the inner shaft to attach the inserter tool to the stop plate. The externally threaded end of the stop plate is engaged with the internally threaded hole of the implant by rotating the outer shaft to attach the stop plate to the implant. The spring is then compressed again to move the second clamping portion away from the first clamping portion, and the implant is removed. The clamping device may further include one or more anti-slipping elements. The anti-slipping elements may be rubber or silicone feet. The clamping device may further include a caddy for storing a stop plate, and the stop plate is removed from the caddy prior to attaching the inserter tool to the stop plate. The fixation element of the implant may be a hole adapted to allow a screw to pass through the implant and engage an adjacent bone surface. The screw may also be included in the system. An open end of the hollow outer shaft of the inserter tool may be sized to fit over the internally threaded end of the stop plate and may be shaped to engage with the exterior of the internally threaded end. The open end and the internally threaded end may both be hexagonal.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

When referring to the drawing, like reference numbers refer to like elements throughout the various figures that comprise the drawing.

DETAILED DESCRIPTION OF THE INVENTION

Figure 1:
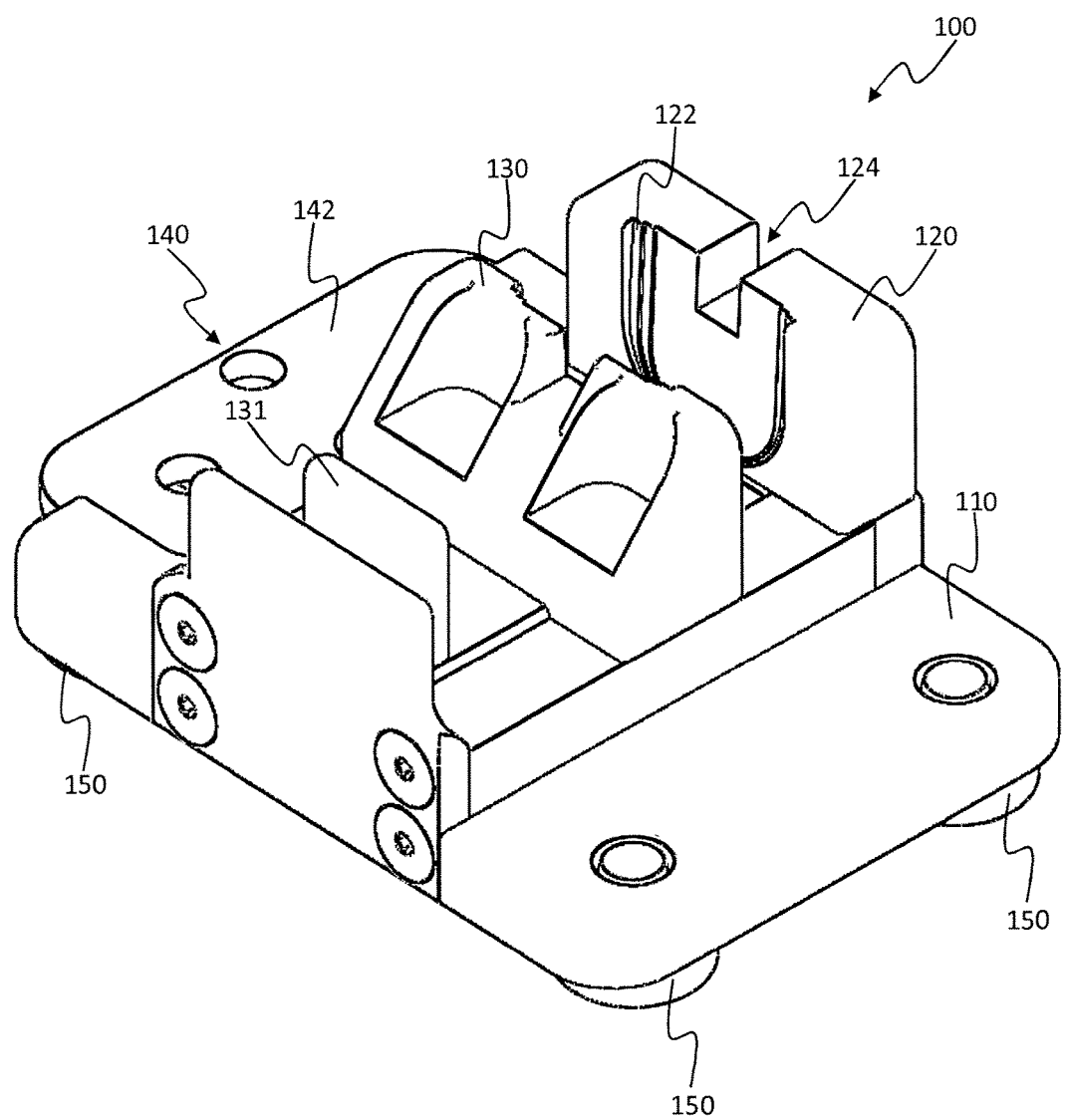
FIG. 1 is a perspective view of a clamping device for affixing a stop plate to an interbody implant according to one embodiment of the present invention.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The terms "subject" or "patient" are used interchangeably. A subject may be any animal, including mammals such as companion animals, laboratory animals, and non-human primates. Human beings are preferred.

The invention provides for a clamping device to aid in the preparation of an interbody implant. The clamping device facilitates affixing a stop plate to an interbody implant. Although the device is described herein specifically in relation to spinal implants, it will be understood that the stop plate clamping device is suitable for use with a variety of medical implants.

Referring to FIGS. 1 and 2A-2C, a clamping device 100 is provided. The clamping device 100 includes a body 110 having a first clamping portion 120, a second clamping portion 130, and a stop plate caddy 140. A stop plate 200 (shown in FIG. 3 and described in more detail below) is stored in the stop plate caddy 140, which is covered by a caddy cover 142. The clamping device 100 may also include one or more anti-slipping elements, such as feet 150 made of rubber or silicone.

The first clamping portion 120 is fixed or movable with respect to the body 110. The first clamping portion 120 may further include a track portion 126 which extends toward the second clamping portion 130. The second clamping portion 130 is movable with respect to the first clamping portion 120 and the body 110. The second clamping portion 130 is attached to the body 110 by a spring 134 (FIG. 2A) and further includes a finger grip 131. The second clamping portion 130 includes an upper portion 136 above the track portion 126 and a bottom portion 138 below the track portion 126. Sandwiching the track portion 126 between the upper portion 136 and the bottom portion 138 maintains the vertical alignment between the first clamping portion 120 and the second clamping portion 130. When a user of the stop plate clamping device 100 pulls back on the finger grip 131, the spring 134 compresses and the second clamping portion 130 moves away from the first clamping portion 120. When the finger grip 131 is released, the spring 134 expands and the second clamping portion 130 moves toward the first clamping portion 120.

Figure 2A:
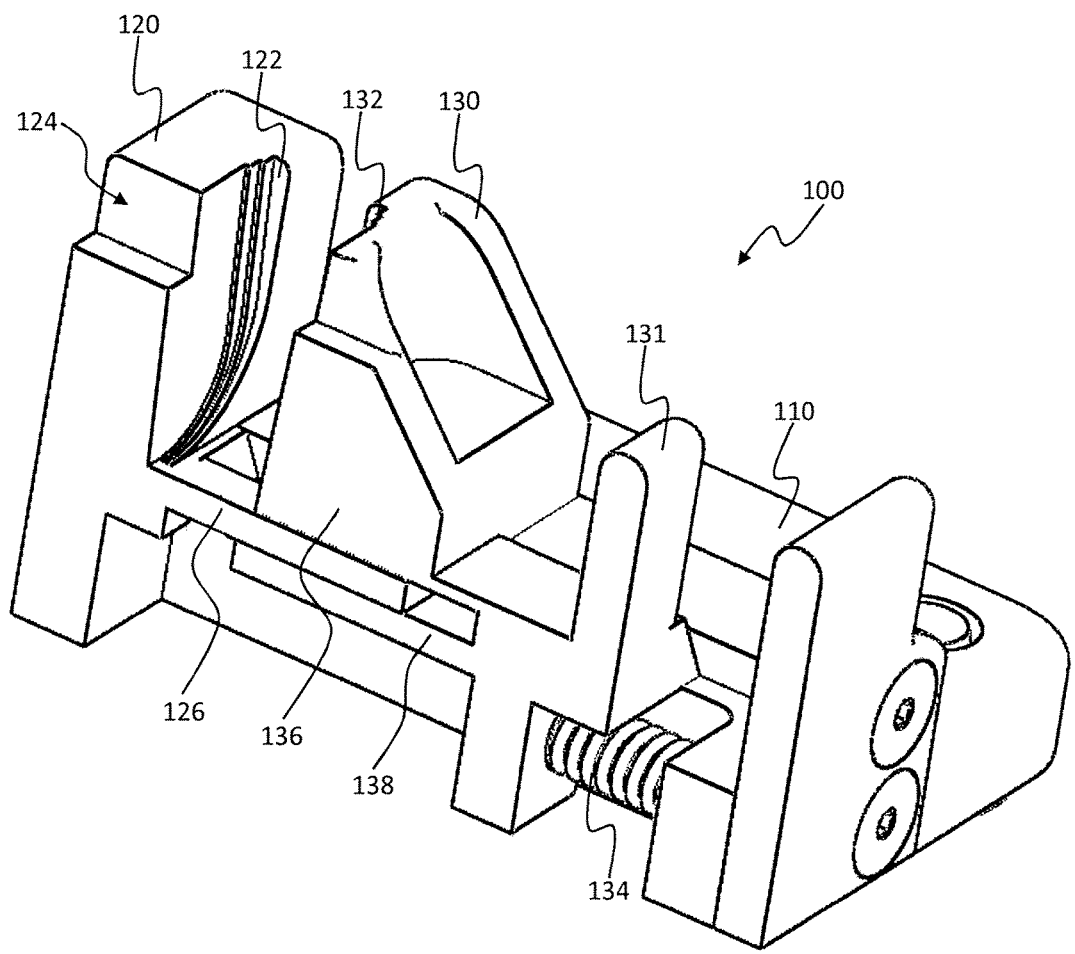
FIG. 2A is a cross-sectional view of the clamping device.
Figure 2B:
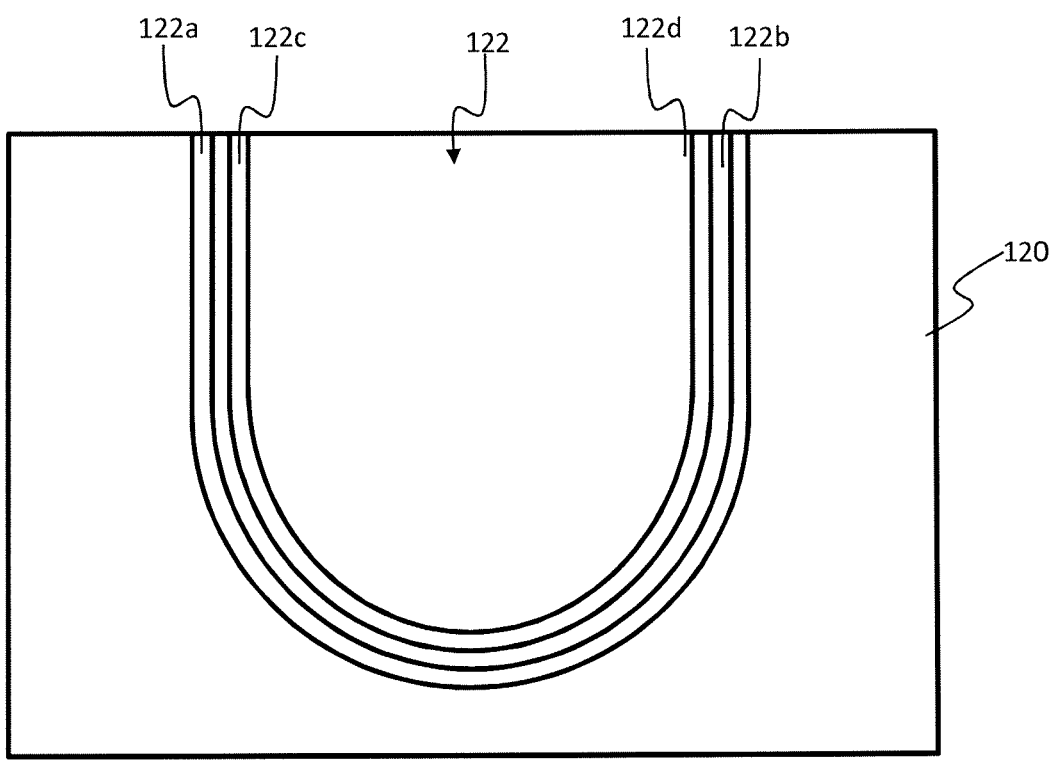
FIG. 2B is a front view of a first stepped seat of the clamping device.
Figure 2C:
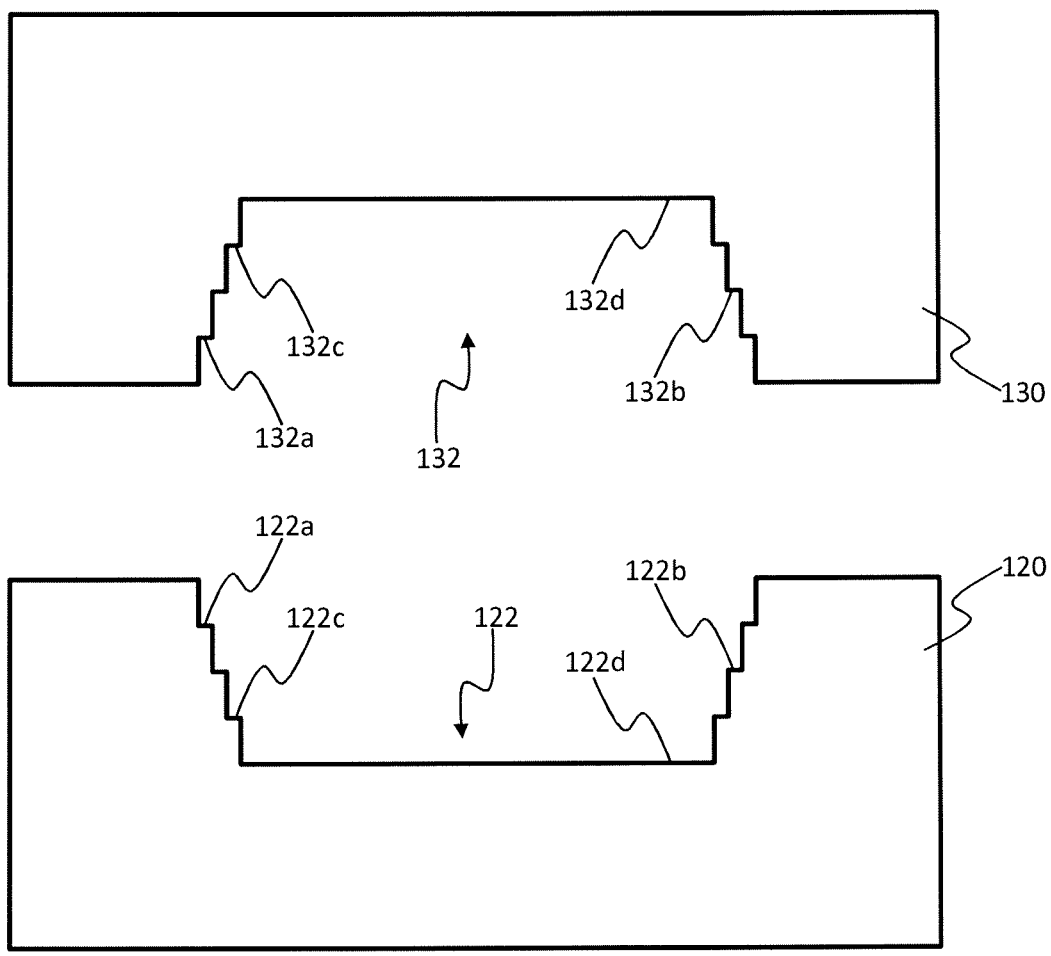
FIG. 2C is a top view of the stepped seats of the clamping device.

The first clamping portion 120 includes a stepped seat 122 and a guide slot 124, and the second portion 130 includes a stepped seat 132. The guide slot 124 may be aligned with the center of the stepped seat 122. The stepped seat 122 is aligned with the stepped seat 132. As described in more detail below, the stepped seat 122, the guide slot 124, and the stepped seat 132 secure and stabilize the implant and the stop plate while affixing the stop plate to the implant. A front view of the stepped seat 122 is depicted in FIG. 2B, and a top view of the stepped seat 122 and the stepped seat 132 is depicted in FIG. 2C. The stepped seat 122 includes a plurality of steps 122a-122d and the stepped seat 132 includes a plurality of steps 132a-132d. The stepped seat 122 and the stepped seat 132 include an equal number of corresponding steps. The stepped seat 122 and the stepped seat 132 are depicted as including four steps, but it will be understood that any number of steps may be included.

Figure 3:
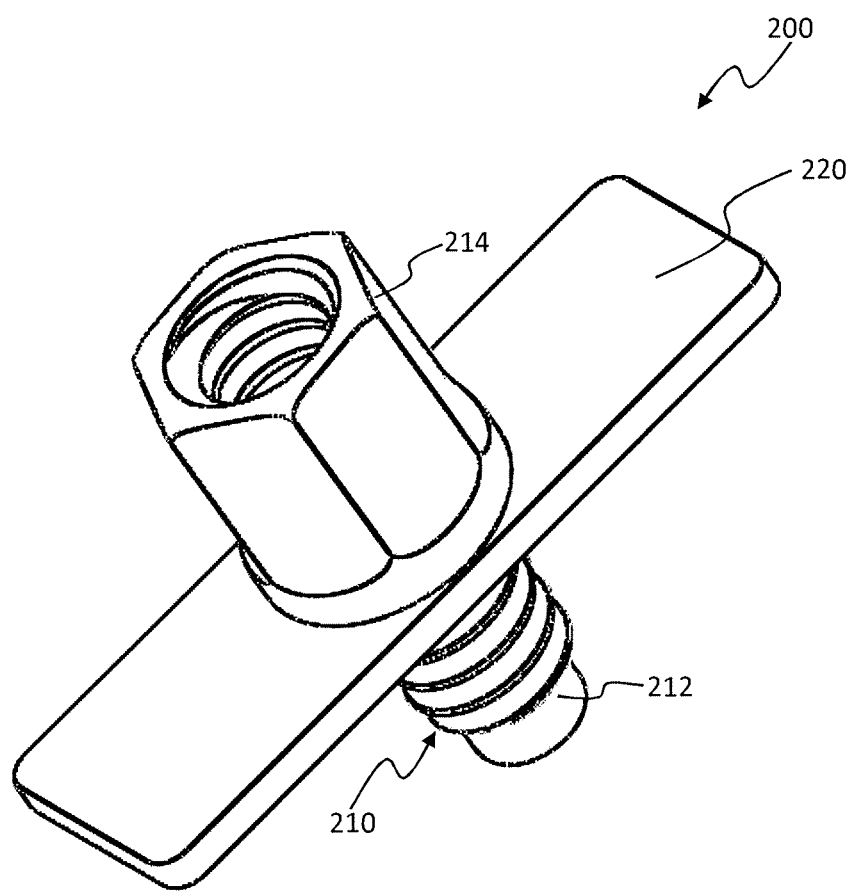
FIG. 3 is a perspective view of a stop plate.

Referring to FIG. 3, the clamping device 100 is used in conjunction with a stop plate 200. Before use, the stop plate 200 may be stored in the stop plate caddy 140. The stop plate 200 includes a central shaft 210 and a free-spinning plate 220 attached to the central shaft 210. The central shaft 210 has two ends on opposite sides of the free-spinning plate 220. A first end 212 is externally threaded and a second end 214 is internally threaded. The second end 214 has an external shape designed to engage with an inserter tool 400, described in more detail below. The second end 214 is preferably hexagonal in cross section. The threads on the first end 212 and the second end 214 are preferably of any suitable pitch and diameter, preferably of a recognized standard. More preferably, the threads on the first end 212 and the second end 214 are 4-40 (i.e., a #4 diameter and 40 threads per inch).

Figure 4A:
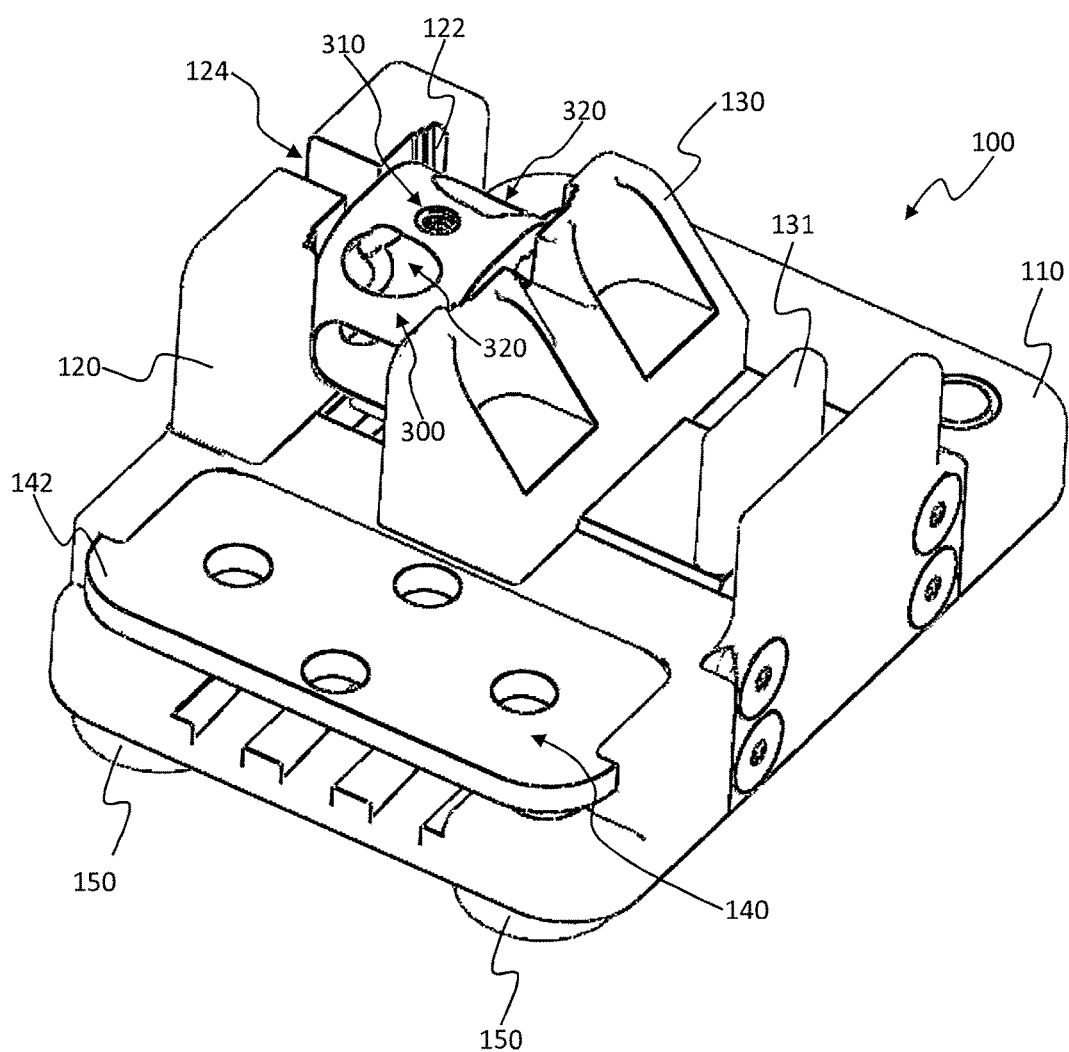
FIG. 4A is a perspective view of mounting an implant in the clamping device.

Referring to FIG. 4A, to affix the stop plate 200 to an implant 300, the implant 300 is first loaded into the clamping device 100 by clamping the implant 300 between the first clamping element 120 and the second clamping element 130. The user of the clamping device 100 loads the implant 300 by pulling back on the finger grip 131 to compress the spring 134 and increase the distance between the first clamping element 120 and the second clamping element 130. The user then places the implant 300 against the stepped seat 122 with the central hole 310 aligned with the guide slot 124. The user then releases the finger grip 131, which expands the spring 134 and brings the stepped seat 132 of the second clamping element 130 in contact with the implant 300.

Figure 4B:
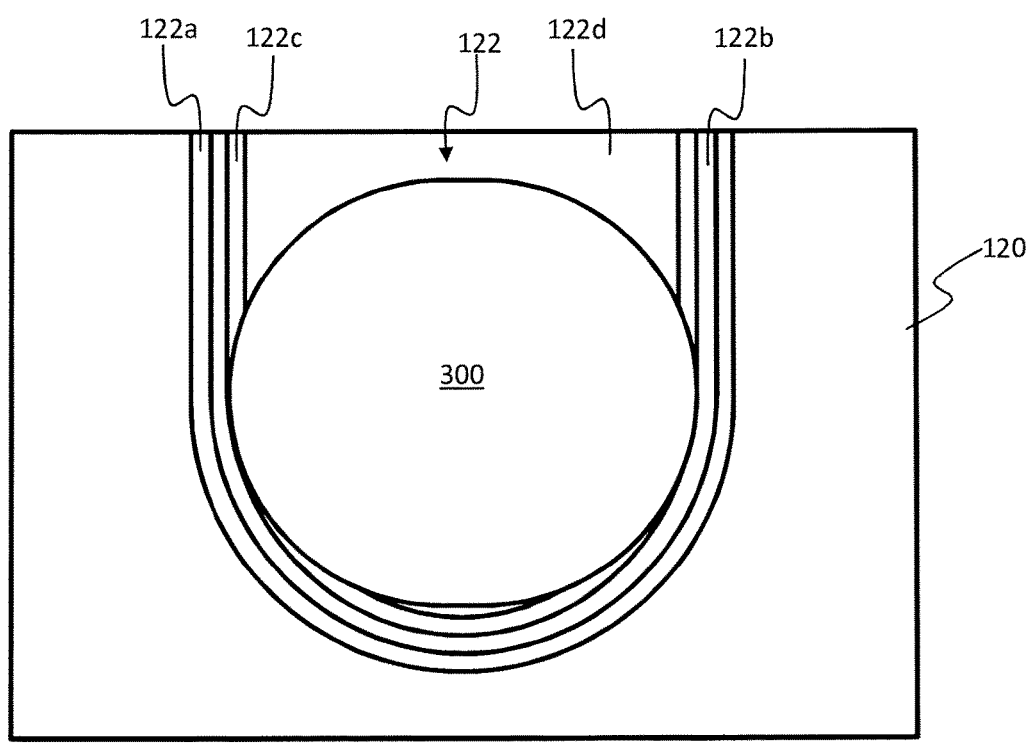
FIG. 4B is a front view of an implant mounted in the first stepped seat of the clamping device.
Figure 4C:
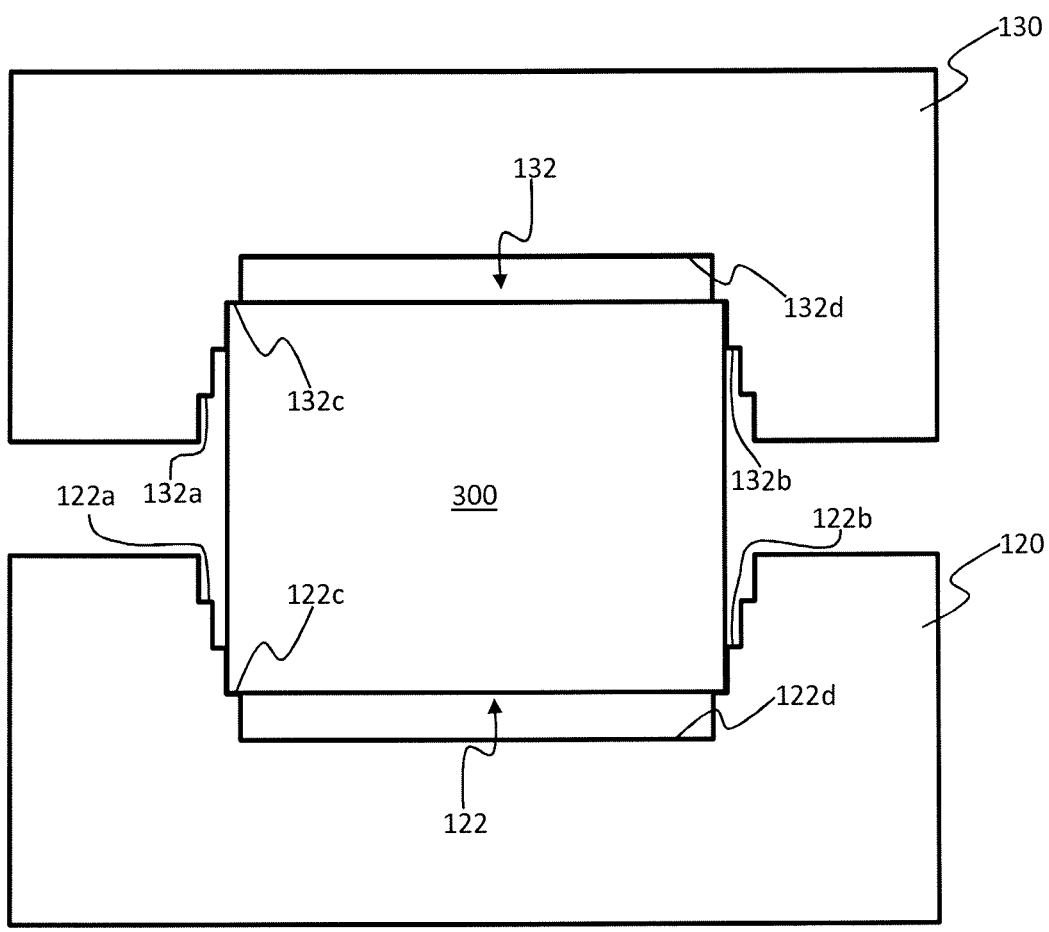
FIG. 4C is a top view of an implant mounted in the stepped seats of the clamping device.

Typically, the size of the implant 300 varies based on the anatomy of the patient and the surgeon is unsure of which size implant is required until the implant 300 is about to be implanted. Accordingly, it is advantageous that the clamping device 100 be able to accommodate implants of different sizes. This is accomplished by the inclusion of the stepped seat 122 and the stepped seat 132. As described above, the stepped seat 122 and the stepped seat 132 each include a plurality of corresponding steps (i.e., steps 122a-122d and steps 132a-132d) of progressively decreasing size. Each pair of corresponding steps fits a different size of implant 300. Accordingly, the user of the clamping device 100 aligns the implant 300 with the corresponding steps, which supports and secures the implant 300. For example, as depicted in FIGS. 4B-4C, the implant 300 fits into the third step 122c. A larger implant 300 would fit into either the first step 122a or the second step 122b, and a smaller implant 300 would fit into the fourth step 122d. The number and shapes of steps included in the stepped seat 122 and the stepped seat 132 depend on the number of possible sizes and shapes of the implant 300. The U-shaped steps depicted in FIG. 4B are best suited for an oval-shaped implant, as depicted, but in other embodiments the steps may have any other suitable shape to best secure the implant 300.

As shown in FIG. 4A, the implant 300 includes a central hole 310 and at least one fixation element 320. In an exemplary embodiment, the at least one fixation element 320 is a hole sized to fit a fixation screw that will attach to bone adjacent to the implant 300. In other embodiments, the fixation screw may be integral with the hole. Other suitable fixation elements 320 include tabs that extend outward from the implant 300. One of ordinary skill in the art will understand that the implant 300 is not limited to any particular fixation element 320. The central hole 310 is internally threaded and is adapted to engage with the externally threaded first end 212 of the stop plate 200.

Figure 5:
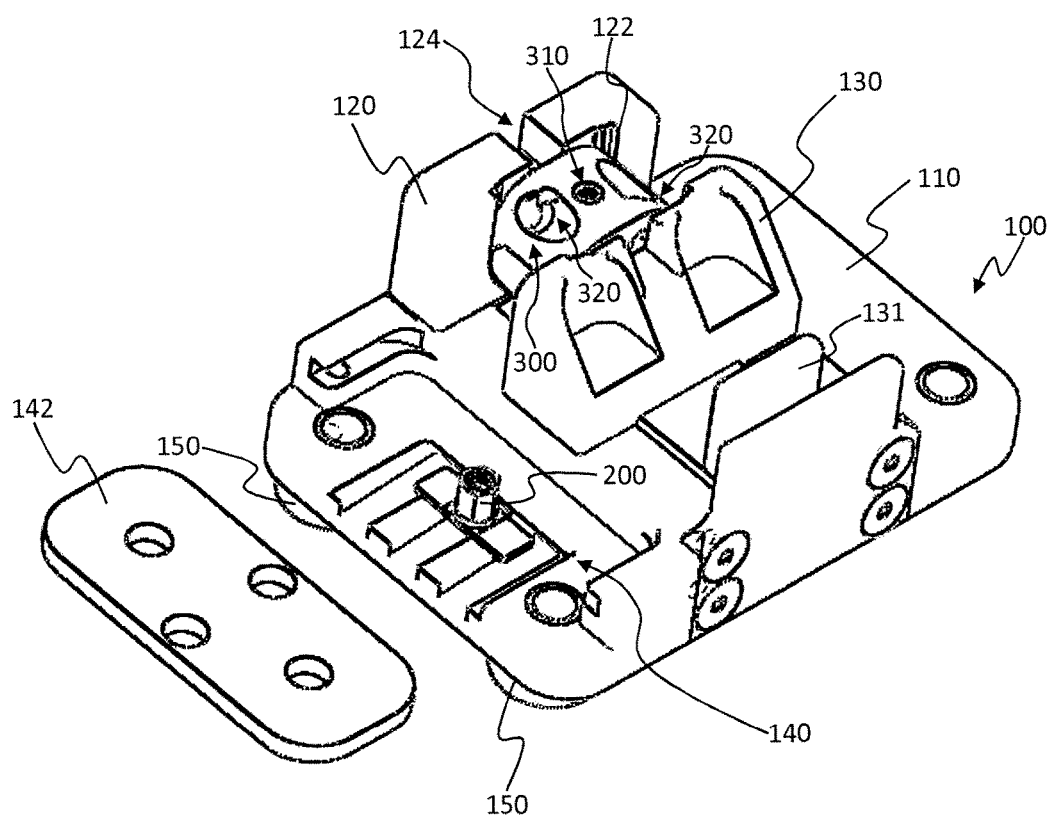
FIG. 5 is a perspective view of the clamping device with the stop plate caddy cover removed.

Referring to FIG. 5, the caddy cover 142 is removed from the stop plate caddy 140 to expose the stored stop plate 200. The caddy cover 142 may be removed either before or after loading the implant 300 into the clamping device 100, but is preferably removed just prior to attaching the stop plate 200 to the implant 300. In some embodiments, the stop plate caddy 140 may store two or more stop plates 200, for example of different sizes or dimensions, in to accommodate the needs of different patients.

Figure 6:
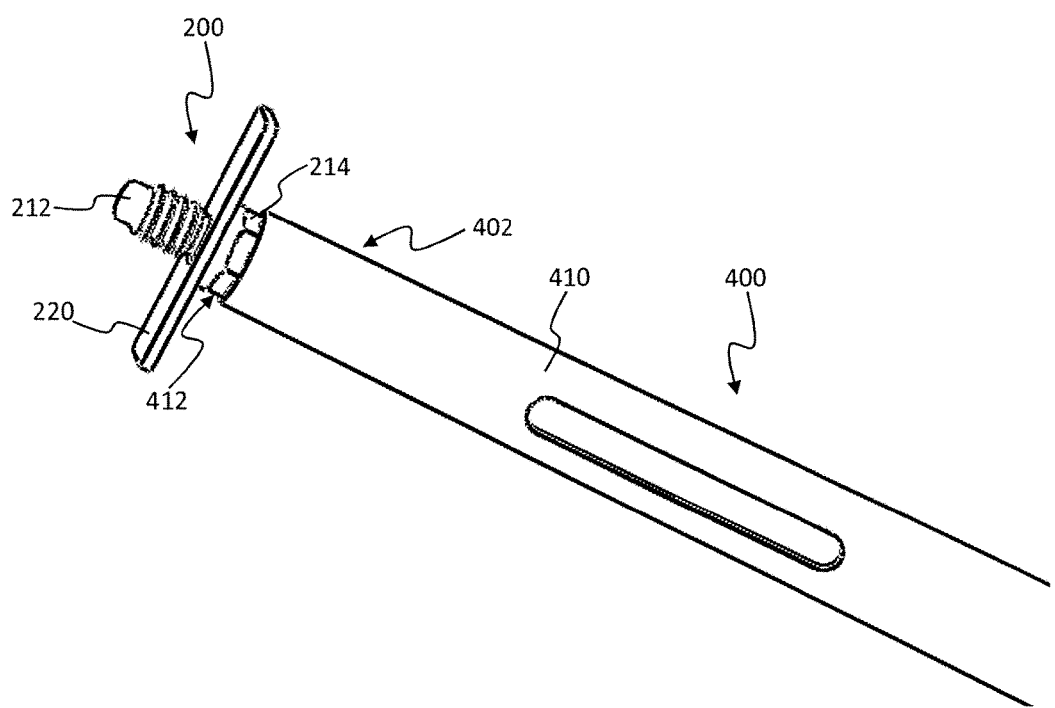
FIG. 6 is a perspective view of the stop plate attached to an implant inserter.
Figure 7:
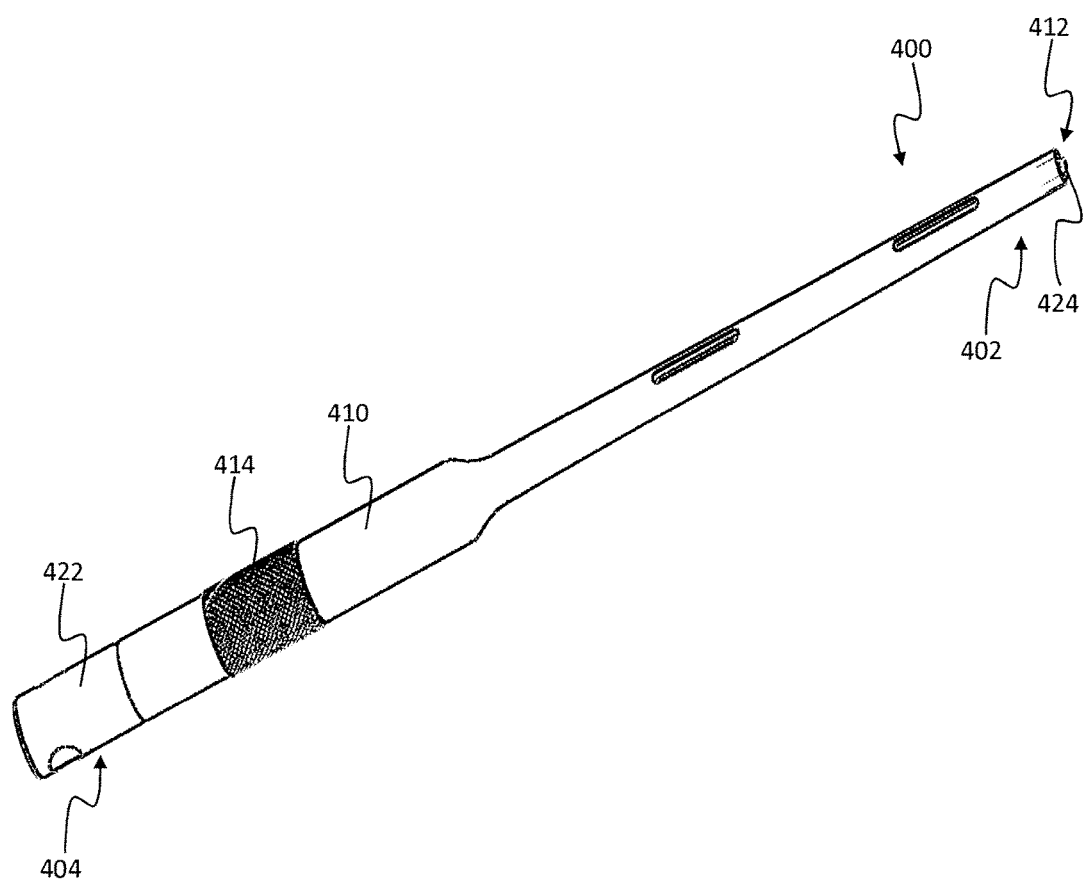
FIG. 7 is a perspective view of the implant inserter.
Figure 8:
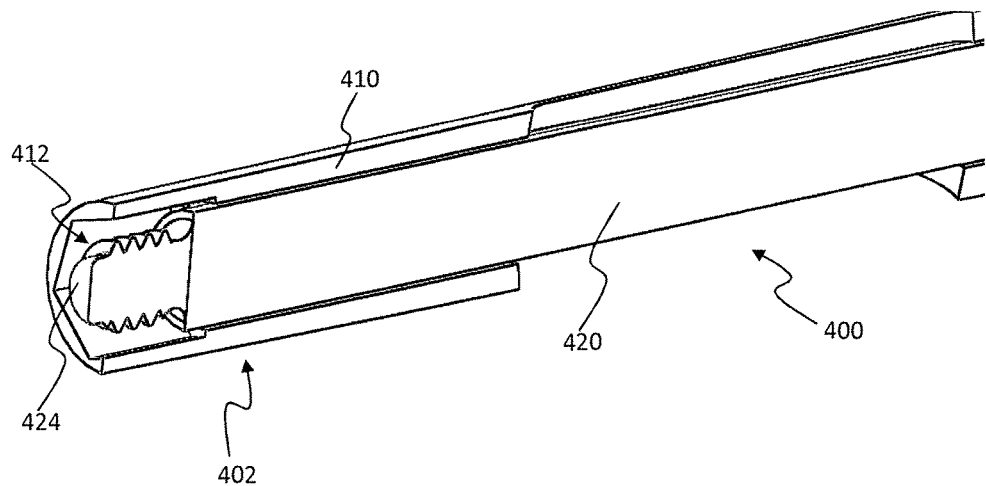
FIG. 8 is a cross-sectional view of the engaging end of the implant inserter.
Figure 9:
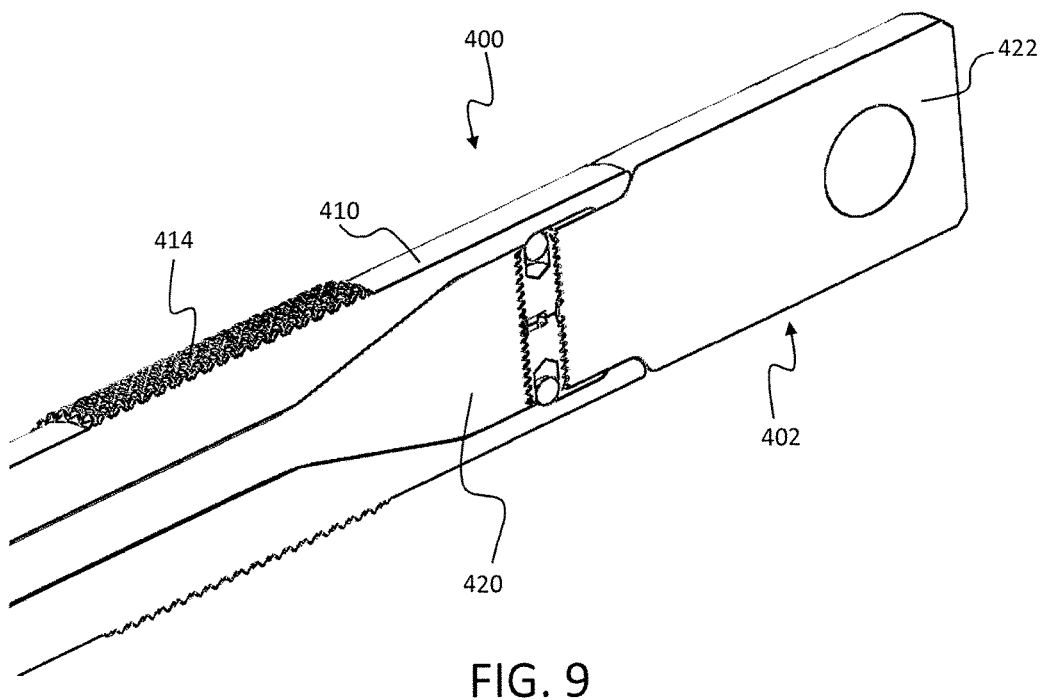
FIG. 9 is a cross-sectional view of the handle end of the implant inserter.

Referring to FIG. 6, the stop plate 200 is removed from the stop plate caddy 140 and attached to an engaging end 402 of the inserter tool 400, shown in more detail in FIGS. 7-9. The inserter tool 400 includes an outer shaft 410 and an inner shaft 420 inside the outer shaft 410. The outer shaft 410 has an open end 412 at the engaging end 402 of the inserter tool 400. The internal diameter of the outer shaft 410 is shaped at the open end 412 to engage with the outer surfaces of the second end 214 of the stop plate 200. The outer shaft 410 may further include a knurled grip 414 to facilitate use of the inserter tool 410. The inner shaft 420 is able to rotate freely within the outer shaft 410 and includes an externally threaded tip 424 at the engaging end 402 of the inserter tool 400. The threads of the externally threaded tip 424 are sized to match the internal threads of the second end 214 of the stop plate 200.

The inserter tool 400 further includes a knob 422 at a handle end 404 which is attached to the inner shaft 420 and extends beyond the outer shaft 410. By rotating the knob 422, the user of the inserter tool 400 is able to rotate the inner shaft 420 with respect to the outer shaft 410. The knob 422 is preferably removably attached to the inner shaft 420 to facilitate easier cleaning of the inserter tool 400. To attach the inserter tool 400 to the stop plate 200, the open end 412 of the inserter tool 400 is fitted over the second end 214 of the stop plate 200, and the knob 422 is rotated to engage the threads of the externally threaded tip 424 with the threads of the internally threaded second end 214. The engagement between the open end 412 and the second end 214 prevents the stop plate 200 from rotating while the externally threaded tip 424 is screwed into the second end 214.

Figure 10:
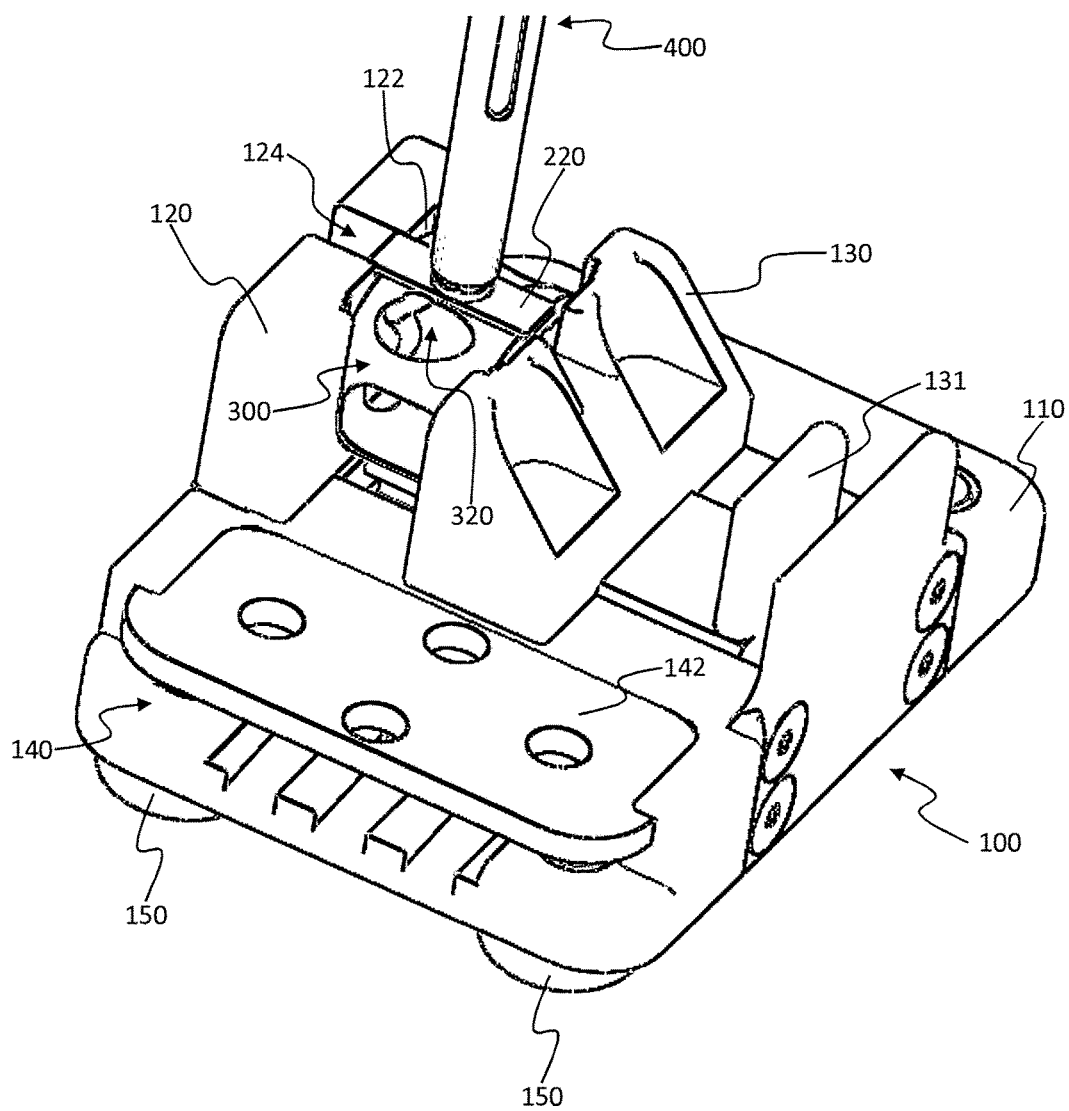
FIG. 10 is a perspective view of the stop plate attached to the implant mounted in the clamping device.

Next, referring to FIG. 10, the stop plate 200 is attached to the implant 300 by screwing the first end 212 of the stop plate 200 into the central shaft 210 of the implant 300. The stop plate 200 is positioned over the implant 300 with the free-spinning plate 220 aligned with the guide slot 124 of the clamping device 100 and the inserter tool 400 is rotated to engage the threads of the first end 212 with the threads of the central shaft 210. Because the free-spinning plate 220 can move with respect to the central shaft 210, the free-spinning plate 220 remains aligned with the guide slot 124 while the inserter tool 400 is rotated. The clamping device 100 secures the implant 300 and prevents rotation while the stop plate 200 is attached to ensure proper alignment.

Figure 11:
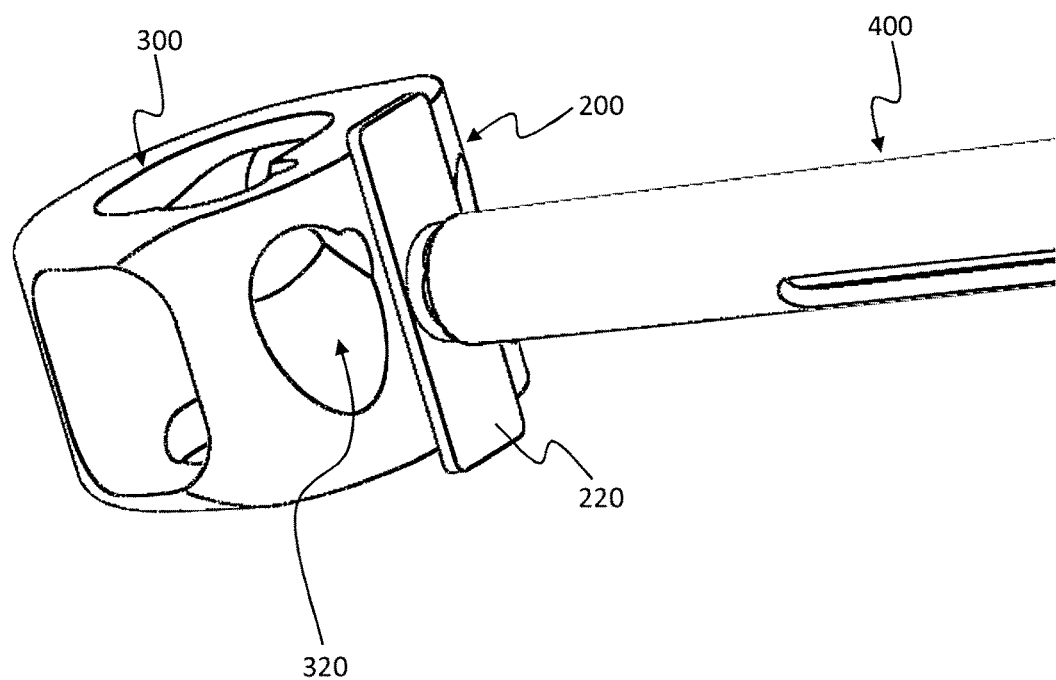
FIG. 11 is a perspective view of the implant attached to the stop plate and the stop plate attached to the implant inserter.

Next, referring to FIG. 11, once the first end 212 is fully engaged with the central shaft 210, the implant 300 is removed from the clamping device 100 by again pulling back on the finger grip 131 to compress the spring 134 and increase the distance between the first clamping element 120 and the second clamping element 130, which releases the implant 300. The implant 300 may then be positioned in space by maneuvering the inserter tool 400.

Figure 12:
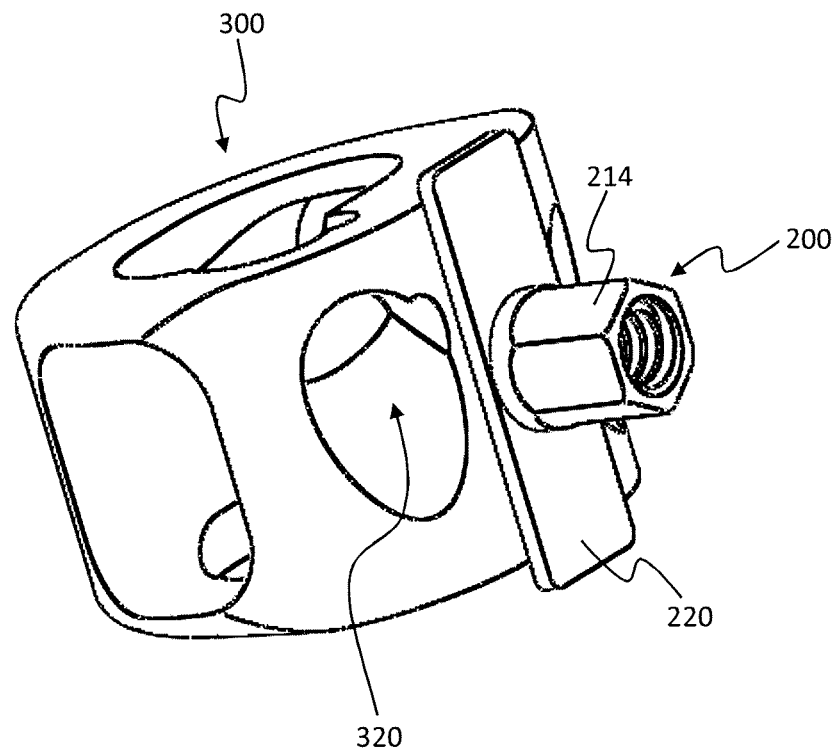
FIG. 12 is a perspective view of the implant attached to the stop plate.

Referring to FIG. 12, once the implant 300 is in the desired position within the patient's body (not shown), the inserter tool 400 can be removed from the stop plate 200 to allow for easier access to the implant 300. The inserter tool 400 is removed by rotating the knob 422, which disengages the threaded tip 424 from the internally threaded end 214. The fixation elements 320 may then be engaged, for example by drilling into adjacent bone through the fixation elements 320 and inserting screws through the resulting holes. While engaging the fixation elements 320, the free spinning plate 220 is in contact with adjacent surfaces, for example the adjacent vertebrae above and below the implant 300, thereby preventing movement of the implant 300.

Figure 13:
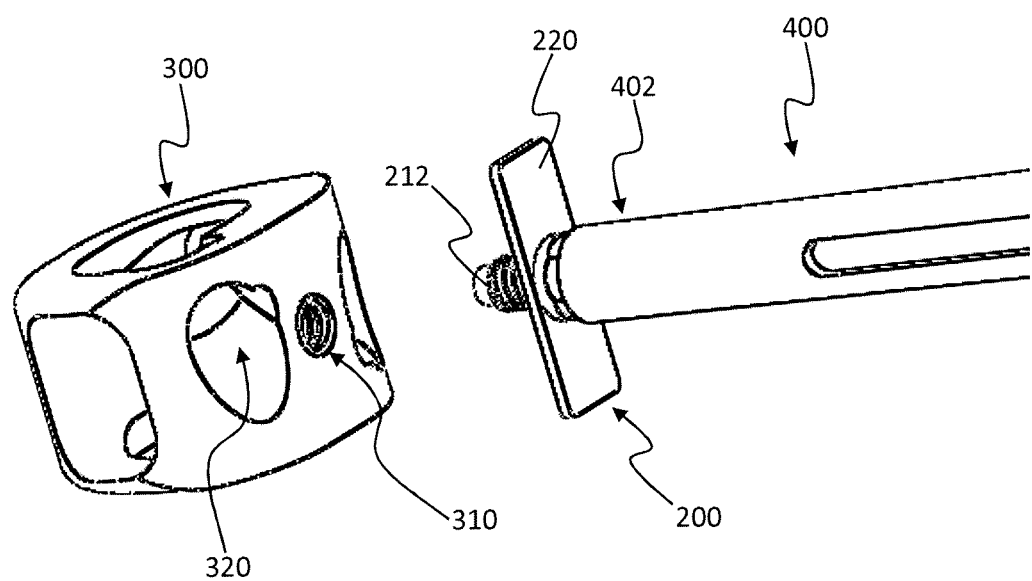
FIG. 13 is a perspective view of the stop plate removed from the implant.

Referring to FIG. 13, once the fixation elements 320 are engaged, the stop plate 200 may be removed by first reattaching the inserter tool 400 to the stop plate 200 and then detaching the stop plate 200 from the implant 300. As described above, the inserter tool 400 may be reattached by rotating the knob 422 while not rotating the outer shaft 410 to engage the threaded tip 424 and the second end 214. Once the inserter tool 400 is attached to the stop plate 200, the stop plate 200 may be detached from the implant 300 by rotating the outer shaft 410 to disengage the first end 214 from the central hole 310.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. It is also expressly intended that the steps of the methods of using the various devices disclosed above are not restricted to any particular order.

What is claimed:

1. A clamping device comprising:
   a body;
   a first clamping portion attached to the body including a guide slot adapted to receive a stop plate;
   a spring; and
   a second clamping portion attached to the body by the spring, the second clamping portion being movable with respect to the first clamping portion,
   wherein the first clamping portion and the second clamping portion each include a stepped seat adapted to secure a variety of differently sized medical implants by clamping an implant between the first clamping portion and the second clamping portion, and
   wherein compressing the spring moves the second clamping portion away from the first clamping portion and expanding the spring moves the second clamping portion toward the first clamping portion.

2. The clamping device of claim 1, further comprising a caddy adapted to store the stop plate.

3. The clamping device of claim 1, wherein the first clamping portion further includes a track portion which extends in the direction of the second clamping portion, and the second clamping portion includes an upper portion above the track portion and a lower portion below the track portion such that sandwiching the track portion between the upper portion and the lower portion maintains a vertical alignment between the first clamping portion and the second clamping portion.

4. The clamping device of claim 1, further comprising one or more silicon or rubber feet adapted to prevent the clamping device from slipping when placed on an adjacent surface.

5. The clamping device of claim 1, wherein the stepped seat of the first clamping portion and the stepped seat of the second clamping portion each include a plurality of steps.

6. The clamping device of claim 5, wherein each of the plurality of steps are U-shaped.

7. The clamping device of claim 5, wherein the plurality of steps of the first clamping portion are identical to and aligned with the plurality of steps of the second clamping portion.

8. The clamping device of claim 7, wherein the plurality of steps of the first clamping portion and the plurality of steps of the second clamping portion progressively decrease in size.

9. The clamping device of claim 1, wherein the stepped seat of the first clamping portion is identical to and aligned with the stepped seat of the second clamping portion.

10. The clamping device of claim 1, wherein the guide slot is aligned with the center of the stepped seat of the first clamping portion.

11. The clamping device of claim 1, wherein the second clamping portion includes a finger grip.

12. The clamping device of claim 11, wherein the second clamping portion is movable with respect to the first clamping portion by pulling or releasing the finger grip.

13. A clamping device comprising:
    a body;
    a first clamping portion attached to the body including a guide slot adapted to receive a stop plate;
    a caddy adapted to store the stop plate;
    a spring;
    a second clamping portion attached to the body by the spring and including a finger grip, the second clamping portion being movable with respect to the first clamping portion by pulling or releasing the finger grip,
    wherein the first clamping portion and the second clamping portion each include a stepped seat adapted to secure a variety of differently sized medical implants by clamping an implant between the first clamping portion and the second clamping portion,
    wherein compressing the spring moves the second clamping portion away from the first clamping portion and expanding the spring moves the second clamping portion toward the first clamping portion, and
    wherein the first clamping portion further includes a track portion which extends in the direction of the second clamping portion, and the second clamping portion includes an upper portion above the track portion and a lower portion below the track portion.

14. The clamping device of claim 13, further comprising one or more silicon or rubber feet adapted to prevent the clamping device from slipping when placed on an adjacent surface.

15. The clamping device of claim 13, wherein the stepped seat of the first clamping portion and the stepped seat of the second clamping portion each include a plurality of steps.

16. The clamping device of claim 15, wherein the plurality of steps of the first clamping portion are identical to and aligned with the plurality of steps of the second clamping portion.

17. The clamping device of claim 15, wherein the plurality of steps of the first clamping portion and the plurality of steps of the second clamping portion progressively decrease in size.

18. The clamping device of claim 13, wherein the stepped seat of the first clamping portion is identical to and aligned with the stepped seat of the second clamping portion.

19. The clamping device of claim 13, wherein the guide slot is aligned with the center of the stepped seat of the first clamping portion.

20. A clamping device comprising:
- a body;
- a first clamping portion attached to the body including a guide slot adapted to receive a stop plate;
- a caddy adapted to store the stop plate;
- a spring;
- a second clamping portion attached to the body by the spring and including a finger grip, the second clamping portion being movable with respect to the first clamping portion by pulling or releasing the finger grip,
- wherein the first clamping portion and the second clamping portion each include a stepped seat adapted to secure a variety of differently sized medical implants by clamping an implant between the first clamping portion and the second clamping portion,
- wherein the stepped seat of the first clamping portion and the stepped seat of the second clamping portion each include a plurality of steps,
- wherein the plurality of steps of the first clamping portion are identical to and aligned with the plurality of steps of the second clamping portion,
- wherein the guide slot is aligned with the center of the stepped seat of the first clamping portion,
- wherein compressing the spring moves the second clamping portion away from the first clamping portion and expanding the spring moves the second clamping portion toward the first clamping portion, and
- wherein the first clamping portion further includes a track portion which extends in the direction of the second clamping portion, and the second clamping portion includes an upper portion above the track portion and a lower portion below the track portion.

* * * * *